(12) United States Patent
Boneh

(10) Patent No.: US 8,192,375 B2
(45) Date of Patent: Jun. 5, 2012

(54) APPARATUS AND METHOD FOR DYNAMICALLY FITTING INSOLES TO A PATIENT

(76) Inventor: Hanan Boneh, Netanya (IL)

( * ) Notice: Subject to any disclaimer, the term of this patent is extended or adjusted under 35 U.S.C. 154(b) by 340 days.

(21) Appl. No.: 12/183,188

(22) Filed: Jul. 31, 2008

(65) Prior Publication Data

US 2010/0030542 A1  Feb. 4, 2010

(51) Int. Cl.
*A61B 5/103* (2006.01)
*A61B 5/117* (2006.01)

(52) U.S. Cl. ........................................ 600/592; 600/587

(58) Field of Classification Search .................... 12/142, 12/146; 33/154, 512, 552; 338/39; 600/587, 600/592; 700/17, 98, 118, 119, 163, 182; 702/152, 156, 168, 170, 179; 703/11
See application file for complete search history.

(56) References Cited

U.S. PATENT DOCUMENTS

| | | | |
|---|---|---|---|
| 4,470,782 A * | 9/1984 | Zimmerman et al. | 425/2 |
| 4,876,758 A | 10/1989 | Rolloff et al. | |
| 5,195,030 A | 3/1993 | White | |
| 5,941,835 A | 8/1999 | Sundman | |
| 6,160,264 A | 12/2000 | Rebiere | |
| 7,047,657 B2 * | 5/2006 | Goeggelmann et al. | 33/552 |
| 7,409,256 B2 * | 8/2008 | Lin et al. | 700/98 |
| 2004/0073399 A1 | 4/2004 | Benson et al. | |
| 2007/0055405 A1 | 3/2007 | Koelling et al. | |
| 2007/0156066 A1 * | 7/2007 | McGinley et al. | 600/587 |

OTHER PUBLICATIONS

Response to Written Opinion in corresponding international application PCT/IL2009/000468.
Written Opinion in corresponding International application PCT/2009/000468 dated Apr. 20, 2011.

* cited by examiner

*Primary Examiner* — Max Hindenburg
*Assistant Examiner* — Charles Becker
(74) *Attorney, Agent, or Firm* — Law Offices of Edward Langer

(57) ABSTRACT

In one aspect, the present invention is directed to an apparatus for dynamically fitting an insole to a patient, the apparatus comprising: a first fitting panel, comprising: a virtual model of desired strains on the plantar surface of a foot; a plurality of fitting units deployed on the first panel, each fitting unit comprising: (a) a strain sensor, for measuring the strain of the foot on the fitting unit; and (b) an elevating unit, for elevating the top point of the fitting unit to a desired point; a processing unit, for instructing the elevating unit to adjust the elevation of the top point of the fitting unit towards a position wherein the strain of the foot, as measured by the strain sensor, corresponds to the strain of the virtual model.

20 Claims, 6 Drawing Sheets

APPARATUS AND METHOD FOR DYNAMICALLY FITTING INSOLES TO A PATIENT

FIELD OF THE INVENTION

The present invention relates to the field of metering devices for orthopedics. More particularly, the present invention relates to an apparatus for dynamically fitting an insole to a patient's foot.

BACKGROUND OF THE INVENTION

Insoles are shoe inserts intended to correct an abnormal, or irregular biomechanics (walking pattern). Foot orthotics is not solely "arch supports," although some people use those words to describe them. It refers also to functions that make standing, walking, and running more comfortable and efficient, by altering slightly the angles at which the foot strikes a walking or running surface, and also by spreading the strain of the body's weight more evenly across the foot.

A partial list of foot conditions that insoles aim at solving are: Achilles Tendonitis, Metatarsalgia (pain near the toes) Sesamoiditis (pain in inner part of the foot), Flat Feet, Neuroma, Arch pain, Heel pain, Pronation, Top of the foot pain, Bunions, Knee pain, Shin pain, Toe pain, back pain, and many more.

The most common foot condition that requires the usage of insoles is Flat feet, also known as pes planus or "fallen arches". Flat feet is a condition in which the arch of the foot collapses. As a result, the entire foot sole has complete—or almost complete—contact with the ground. Additionally, in some individuals (an estimated 20-30% of the general population) the arch simply never develops in one foot (unilaterally) or both feet (bilaterally).

Insoles furthermore are often the sovereign remedy for heel pain. Heel pain is generally a sign of heel spurs (also known as planter fasciitis) normally caused by a biomechanical imbalance. Over a period of time, this imbalance creates tension in the foot's planter fascia region, thus resulting in heel pain.

Corns, yet another common but painful foot problem, represent calluses in an advanced form. A callus is a portion of skin that, after repeated exposure to pressure, thickens uncomfortably. Once a callus exists long enough to accumulate dead tissue at its core, it becomes a corn. Properly fitted insoles reduce the risk of developing corns.

One prior art technology for handling the above mentioned issues and others comprises adjusting a mould of a patient's plantar surface in order to produce a corresponding insole (orthotics). The mould can be obtained by placing a foot in foamed polyurethane, gypsum, and the like. The mould is taken either by the patient standing on the designated surface (foamed polyurethane), or while the patient is sitting and the mould is then fitted to the foot using bandages (gypsum).

In a further development, the orthopedic technician takes a picture of the plantar surface of the patient's foot. The picture of the plantar surface is obtained by a scanner, which operates on the same general principles as an office scanner. The patient places his foot on a flat glass surface, and a camera scans the foot underneath. The outlines of the foot are generated by software means. The technician then places necessary corrective modules on the outlined model (heel cap, metatarsal support, supinating or pronating wedges, retro-capital support, etc.), and the resulting files are transferred to a center for producing corresponding insoles.

The drawback in all the above technologies, and in fact in all known technologies for insoles fitting, is that the foot is placed on a flat surface and as such, the produced information is partial, as it provides no map of the strains. The same can be said regarding the gypsum mould that is taken when the patient seats, and therefore does not simulate the real life condition.

It is an object of the present invention to provide an apparatus for dynamically fitting an insole to a patient, which overcomes the abovementioned drawbacks, and others, of the prior art.

Other objects and advantages of the invention will become apparent as the description proceeds.

SUMMARY OF THE INVENTION

The following embodiments and aspects thereof are described and illustrated in conjunction with systems, tools methods, and so forth, which are meant to be merely illustrative, not limiting in scope.

The term "strain" refers in the text and claims herein to any expression of weight.

By using an insole, the deployment of the strains on the foot thereof is changed. For example, lifting the surface of the insole in a certain point increases the strain on this point. This way the deployment of strains of a foot can be changed in order to correspond to a "healthy" foot.

In one aspect, the present invention is directed to an apparatus for fitting an insole to a patient, the apparatus comprising: a first fitting panel, comprising: a virtual model of desired strains on the plantar surface of a foot; a plurality of fitting units deployed on the first panel, each fitting unit comprising: (a) a strain sensor, for measuring the strain of the foot on the fitting unit; and (b) an elevating unit, for elevating the top point of the fitting unit to a desired point; a processing unit, for instructing the elevating unit to adjust the elevation of the top point of the fitting unit towards a position wherein the strain of the foot, as measured by the strain sensor, corresponds to the strain of the virtual model.

In one aspect, the present invention is directed to an apparatus for fitting an insole to a patient, the apparatus comprising: a first fitting panel, comprising: a virtual model of desired strains on the plantar surface of a foot; a plurality of fitting units deployed on a first panel, each fitting unit comprises: (a) a strain sensor, for measuring the strain of the foot on the fitting unit; and (b) an elevating unit, for elevating the top point of the fitting unit to an elevation wherein the strain of the foot as measured by the strain sensor corresponds to the strain of the virtual model.

The apparatus may further comprise a second fitting panel in the structure of the first, for enabling fitting insoles to feet of different length.

The apparatus may further comprise a unit for producing an insole.

According to one embodiment of the invention, the first fitting panel further comprises elevated edges, for placing the foot in a predefined position on the panel.

According to another embodiment of the invention, the position of the foot on the panel is detected by computerized means.

The elevating unit comprises a piston operated by pneumatic means, hydraulic means, or any other means used for this purpose.

The apparatus may further comprise a user interface, for adjusting a designed insole.

The apparatus may further comprise a display, for displaying information selected from a group comprising: measured strains, designed insole.

The apparatus may further comprise a pad, preferably of flexible material, placed on the fitting units.

According to one embodiment of the invention, each of the fitting units comprises on the top thereof a platform movable along a bearing, thereby fitting the position of the platform according to the plantar surface thereof According to one embodiment of the invention, the fitting units are deployed in a matrix order.

According to one embodiment of the invention, the deployment of the fitting units corresponds to the plantar surface of a common patient.

The virtual model may be selected from a library of virtual models. Preferably, a virtual model is generated by employing variables such as identification of an orthopedic problem, foot size, left foot or right foot, and so on.

In another aspect, the present invention is directed to a method for fitting an insole to a patient, the method comprising the steps of: providing a model of desired strains of the plantar surface of a patient; repeating the process of: (a) comparing the strain on each of a plurality of points of the plantar surface of a patient with that of the corresponding point of the model; (b) adjusting the elevation of the surface on which the patient stands towards a position wherein the measured strain will correspond to said model; until the strain of all points correspond to the strain of the corresponding point in the model.

In yet another aspect, the invention is directed to a method for fitting insoles to a patient, the method comprising the steps of: providing a model of desired strains of the left and right plantar surfaces of a patient; adjusting the elevation of the plantar surfaces on which the patient's feet stand until the total strains of the left foot equals that of the right foot; for each foot repeating the process of: (a) comparing the strain on each of a plurality of points of the patient's plantar surface with the strain of the corresponding point of the model; (b) adjusting the elevation of the surface on which the patient stands towards a position wherein the measured strain will correspond to said model; until the strain of all points corresponds to that of the corresponding point in the model.

According to one embodiment of the invention, the adjustment is carried out by increasing the elevation in the event the measured strain of a point is less than the corresponding strain of the model, and vice versa.

In addition to the exemplary aspects and embodiments described above, further aspects and embodiments will become apparent by reference to the figures and by study of the following detailed description.

BRIEF DESCRIPTION OF THE DRAWINGS

The objects and features of the present invention will become apparent from the following detailed description considered in conjunction with the accompanying drawings, in which.

Figure 1:
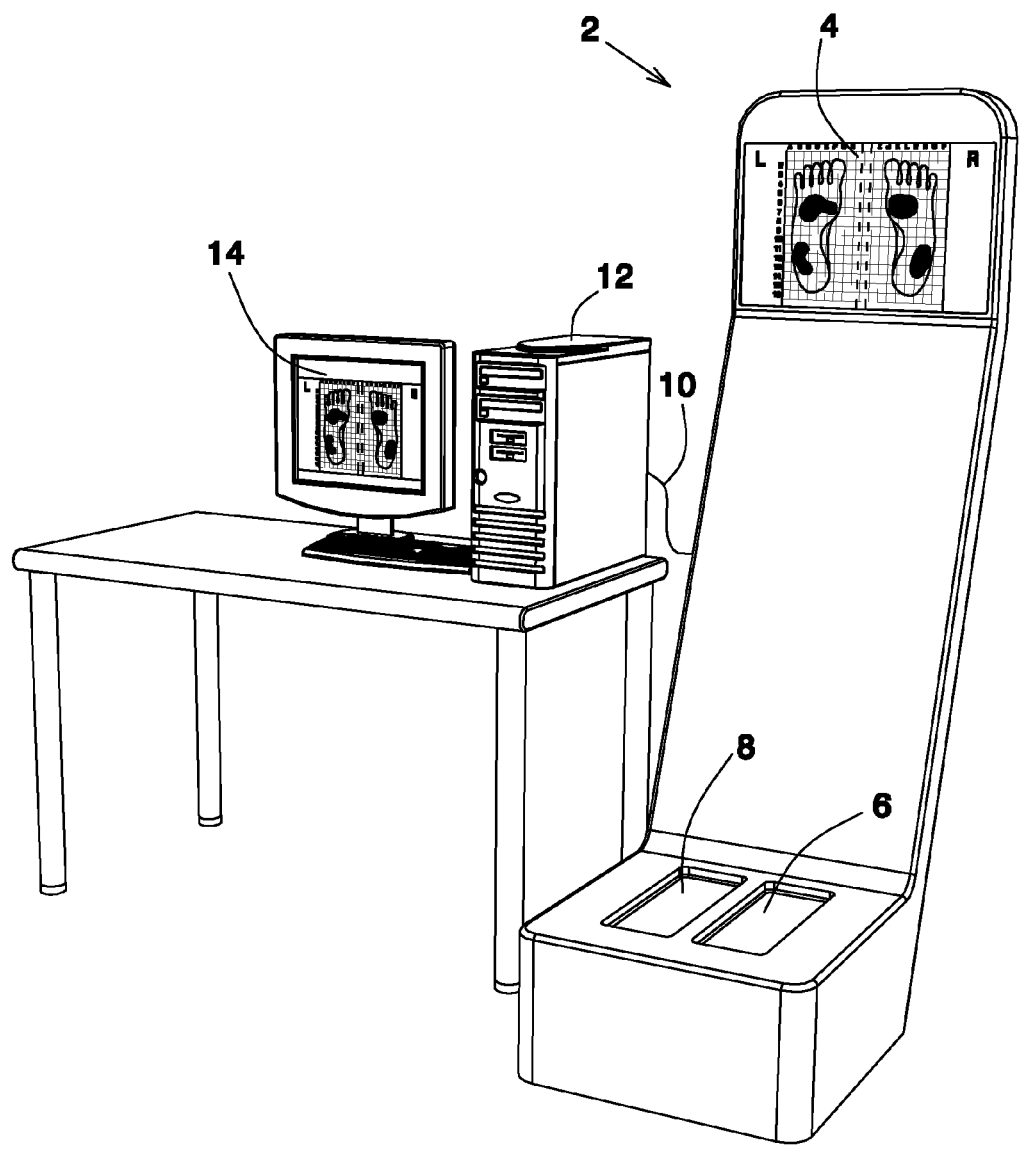
FIG. 1 schematically illustrates an apparatus for fitting an insole to a patient's feet, according to embodiments of the present invention.

It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, are merely intended to conceptually illustrate the structures and procedures described herein. Reference numerals may be repeated among the figures in order to indicate corresponding or analogous elements.

DETAILED DESCRIPTION OF PREFERRED EMBODIMENTS

In the following detailed description, numerous specific details are set forth in order to provide a thorough understanding of the invention. However, it will be understood by those skilled in the art that the present invention may be practiced without these specific details. In some instances, well-known methods, procedures, components and circuits have not been described in detail, for the sake of brevity.

FIG. 1 schematically illustrates an apparatus for fitting an insole to a patient's feet, according to embodiments of the present invention.

The apparatus, marked herein by numeral 2, comprises two fitting panels 6 and 8, a display 4, and a processing unit, embodied herein by a computer 12.

The object of each of fitting panels 6 and 8 is to fit an insole to the feet placed on the panel, such that the strains of each point of the panel will correspond to the strain of a virtual model.

The term "virtual model" refers herein to information of a desired strain on each point of the plantar surface thereof, while the patient thereof stands.

A virtual model can take in consideration input variables such as specific orthopedic problems, foot size, left foot or right foot, and so forth.

A virtual model can be provided to a device as a matrix (such as a Digital Terrain Model), a function, a strain map, and so on. Generating a virtual model may be carried out by interpolation means for calculating information between data points, and so on.

A virtual model can be stored in a library of virtual models.

A display 4 is used for displaying to a patient or operator information of the sampled feet, the designed insole, and so on. The display may also comprise virtual buttons as part of a user interface, and so on.

In order to measure the strains on a patient's sole, the patient stands on the apparatus such that his left foot is placed on fitting panel 8, and his right on fitting panel 6.

Figure 2:
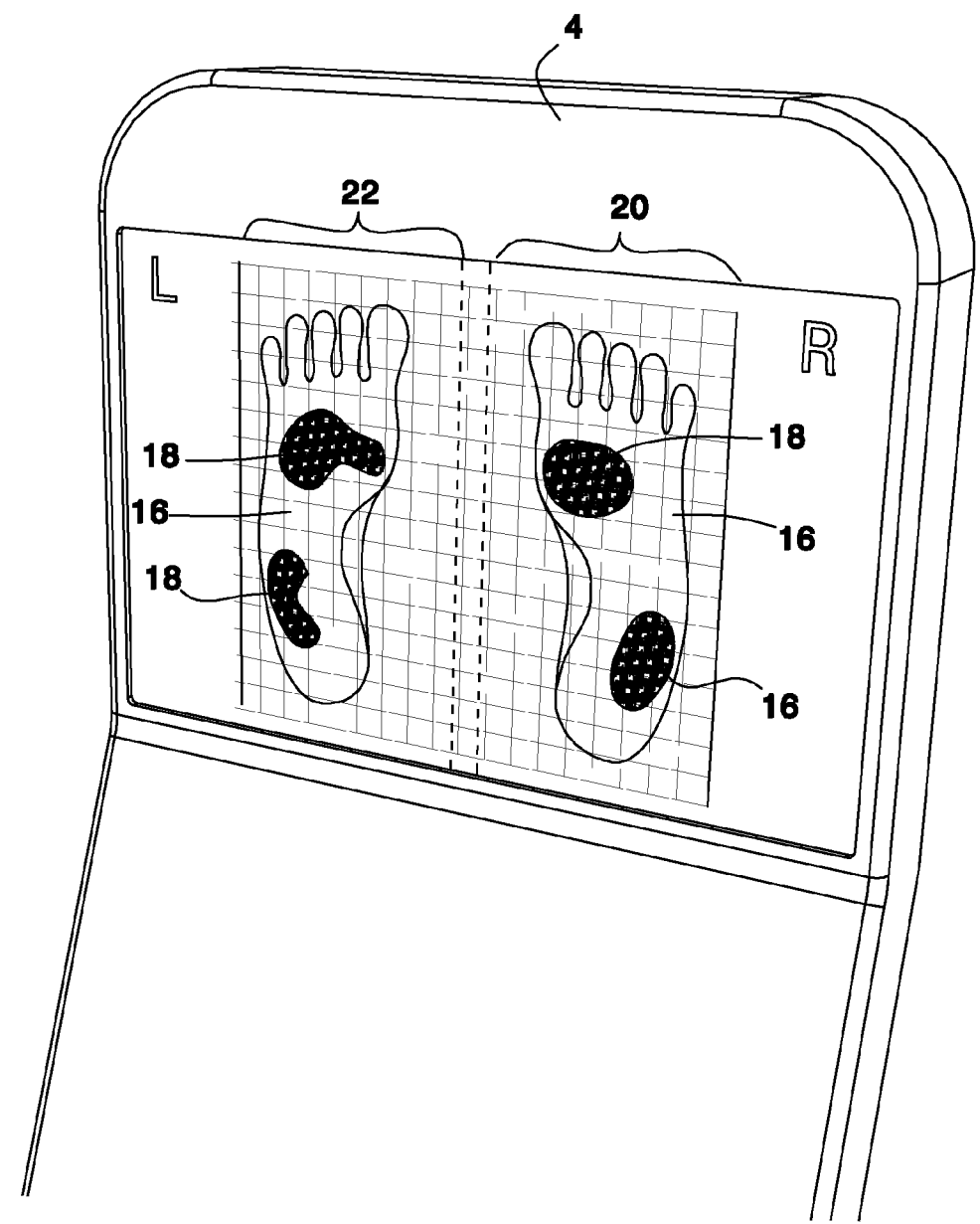
FIG. 2 schematically illustrates a presentation of a digitized plantar surface of a patient, according to one embodiment of the invention.

FIG. 2 schematically illustrates a presentation of a digitized plantar surface of a patient, according to one embodiment of the invention.

The presentation illustrates a digitized image 16 of the plantar surface of the feet (soles) of the patient. Regions 18, which are displayed in a different texture/color than region 16, denote disorders on the strains of the patient's sole.

Over-strains and under-strains may be marked by different textures. For example, white color may denote normal strain on the foot, red color over strain, blue color under strain, and black color, background.

The letters "R" and "L" denote which of the schemes refers to the right foot, and which to the left foot.

Figure 3:
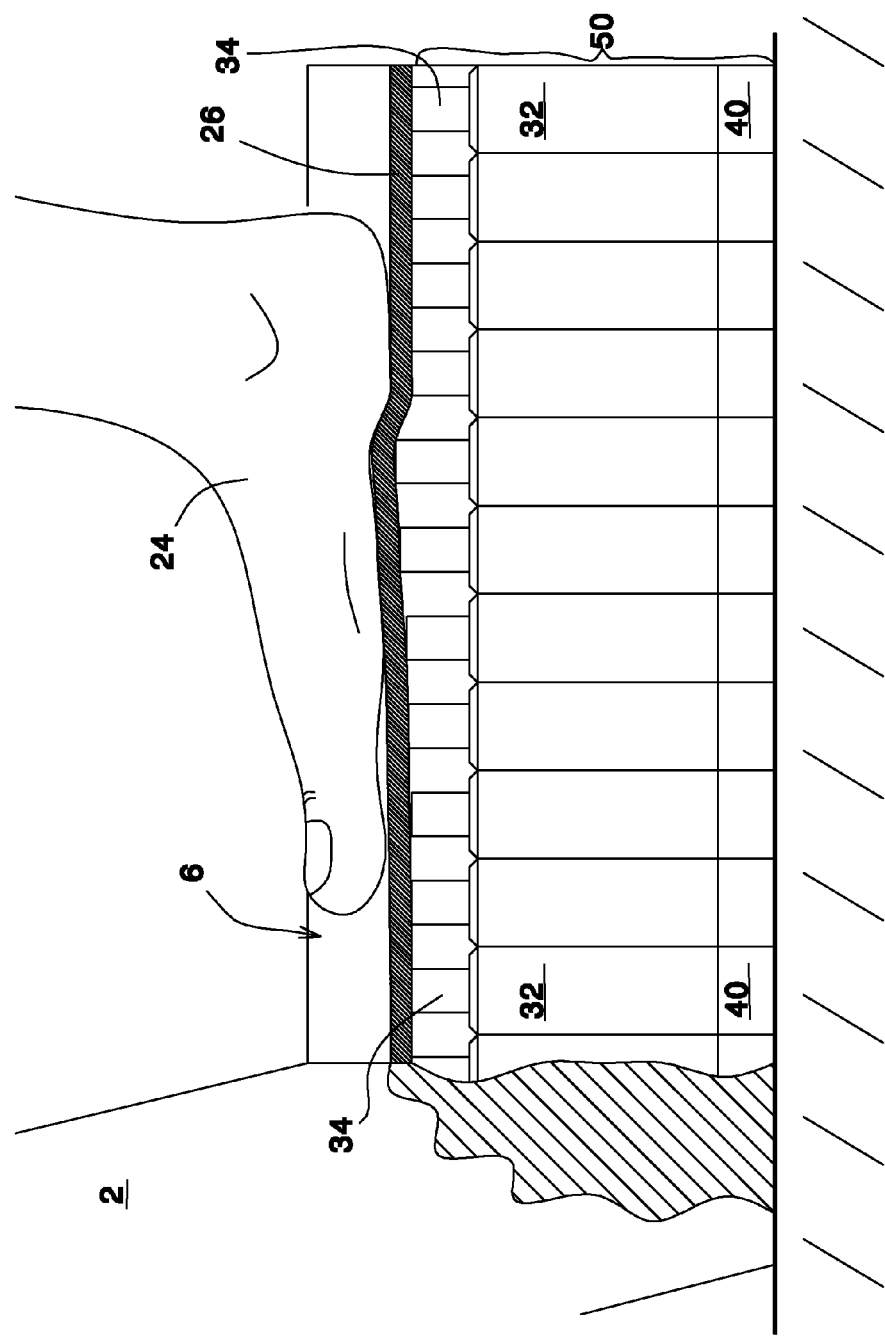
FIG. 3 is a sectional view which schematically illustrates the structure of a fitting panel (marked by numeral 6 and 8), according to one embodiment of the invention.

FIG. 3 is a sectional view which schematically illustrates the structure of a fitting panel (marked by numerals 6 and 8), according to one embodiment of the invention.

According to this example, each of the fitting panels 6 and 8 comprises a matrix of fitting units 50. The structure of each fitting unit is detailed in FIG. 4.

It should be noted that other deployments than matrix of the fitting units might be used. For example, the deployment of the fitting units might be directed to points wherein a strain is higher or lower relative to other points of the plantar surface, i.e., the deployment corresponds to the structure of the plantar surface of a "common" patient.

As FIG. 3 is a side view, only one column of the matrix is seen.

Above the matrix of fitting units is placed a pad 26, preferably of flexible material.

Figure 4:
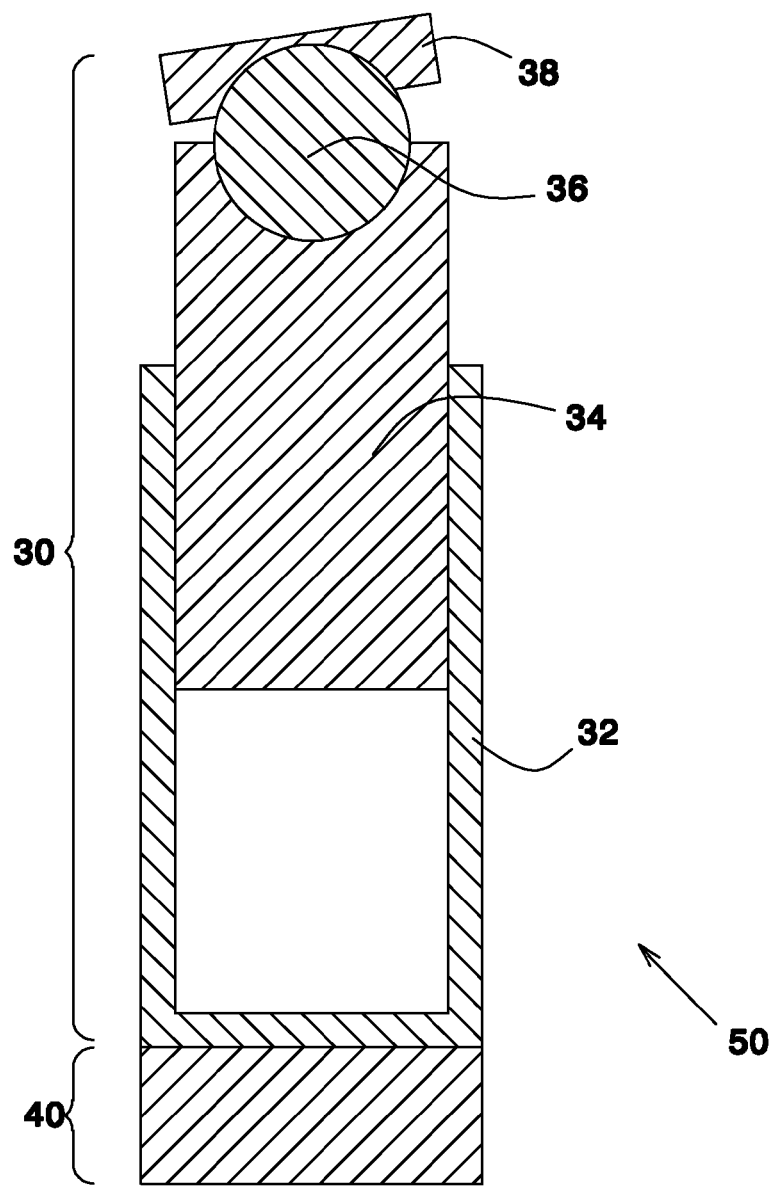
FIG. 4 schematically illustrates a structure of a fitting unit 50, according to one embodiment of the invention.

FIG. 4 schematically illustrates a structure of a fitting unit 50, according to one embodiment of the invention.

Each fitting unit 50 comprises an elevating unit 30 and a strain sensor 40, such as a strain gauge.

The object of fitting unit 50 is to bring the strain caused by a foot to correspond to the strain of the corresponding point of a virtual model thereof In order to achieve this objective, the elevation of the surface underneath is changed, until it reaches the desired strain.

A strain gauge is a device used to measure the strain of an object. The most common type of strain gauge consists of an insulating flexible backing, which supports a metallic foil pattern. The gauge is attached to the object by a suitable adhesive, such as superglue. As the object is deformed, so is the foil, causing its electrical resistance to change.

A strain gauge is one example of strain sensor. Those skilled in the art will appreciate that other technologies for measuring strain may be employed, such as weight meters. Thus, the term "strain" refers herein to any expression of weight. Accordingly, a strain sensor is a sensor capable of measuring weight.

According to this embodiment of the invention, an elevating unit 30 moves the top thereof to a desired elevation. It comprises a cylinder 32, and a piston 34 therein. The piston is the movable element. The operating mode can be by pneumatic means, hydraulic means, and the like.

According to this embodiment of the invention, the top of each fitting unit comprises a platform 38, which is placed on a ball 36 disposed on piston 34. The angle of platform 38 is adjusted by the structure of the foot on the fitting panel in the contact location thereof. Thus, the ball operates as a bearing.

Fitting Insoles to a Patient

Figure 5:
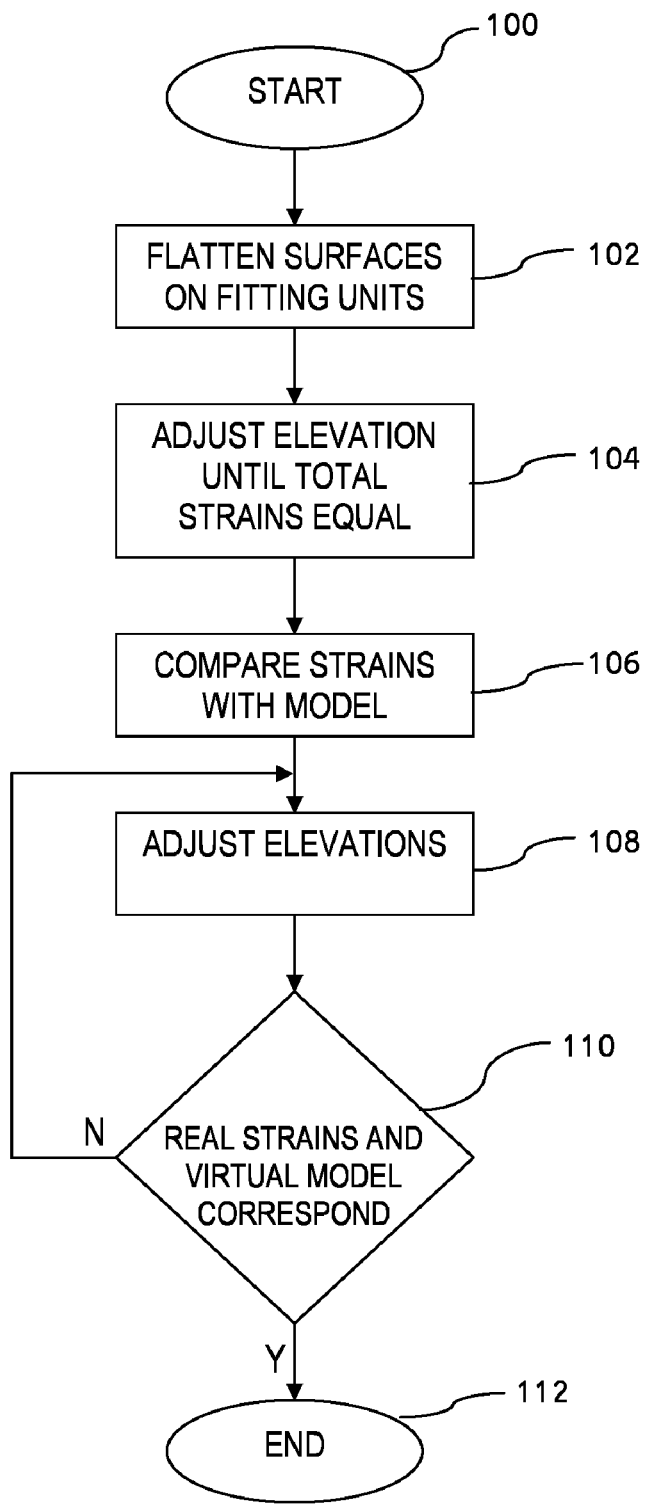
FIG. 5 schematically illustrates a process of fitting insoles to a patient, according to one embodiment of the invention.

FIG. 5 schematically illustrates a process of fitting insoles to a patient, according to one embodiment of the invention.

The process starts at block 100, wherein the patient stands on the fitting panels (not shown in this figure, but marked in other figures by numerals 6 and 8) of the fitting apparatus (not shown in this figure, but marked in other figures by numeral 2).

At block 102, each fitting panel moves its elevating units to the same elevation, thereby generating by platforms 38 thereof a flat surface.

At block 104, the elevation of each of the surfaces is adjusted until the total strains of the left fitting panel 8 is equal to this of the right fitting panel 6.

For people whose feet are not of equal length, elevation of the left surface might differ from that of the right, and accordingly this stage enables to calculate the additional portion to the elevation of the shorter foot.

The level of one surface can be adjusted by changing the elevation of platforms (not shown in this figure, but marked in other figures by numeral 38) thereof by the same portion. The change may be calculated by the difference between the elevation of left and right surfaces.

The process of this step should be repeated until reaching equality between the total strains on the left and right surfaces.

At block 106, the strain on each of the strain sensors of the fitting panels is compared to the corresponding strain of a virtual model of a foot. Thus, there is at least one pair of virtual models of "healthy feet", one for the left foot, and one for the right. Each virtual model comprises the desired strain on each element of its matrix. Accordingly, there may be a plurality of pairs of models, each for a different size of feet, different weight of the person, and so on.

At block 108, each elevating unit changes its elevation according to the difference between the actual and virtual strains thereof At block 110, the correspondence between the real and virtual models is questioned. If the elevation of at least one of the fitting units must be adjusted, then the process repeats from step 108; otherwise, the process continues with step 112.

Figure 6:
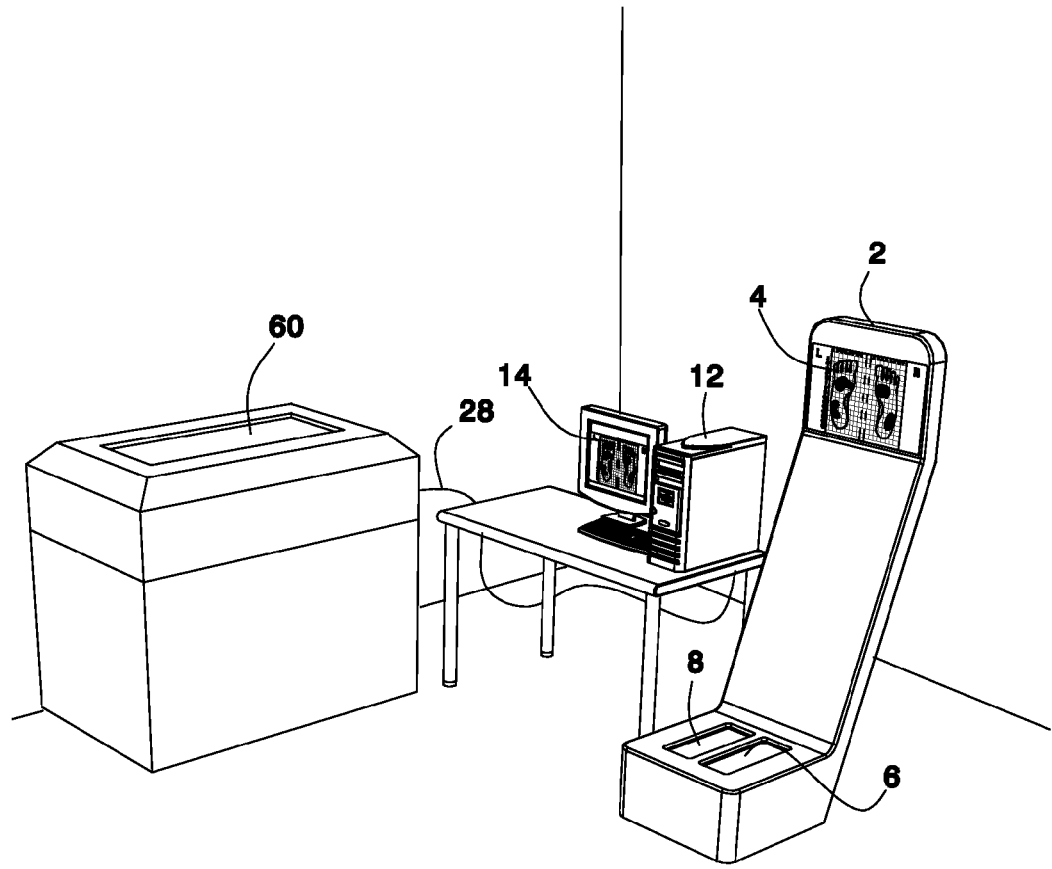
FIG. 6 schematically illustrates an apparatus for fitting an insole to a patient's feet, according to embodiments of the present invention.

At block 112, a virtual model of the insoles of the patient can be stored in a file, and provided to a unit that produces insoles according to this file, such as apparatus 60 on FIG. 6.

As such, the method described in the block diagram of FIG. 5 fits insoles for both feet, left and right. However, it should be noted that a fitting apparatus as described herein may comprise a single fitting panel, and accordingly fit the insole of each foot separately. Fitting insoles for both feet enables taking into consideration the difference in the length of the feet, which characterizes some people.

In a further embodiment of the present invention, apparatus 2 comprises means for adjusting the generated model of the insoles, for example, in order to cure plantar disorders. The adjusting operation may be carried out by increasing or decreasing certain regions of a virtual model of the insoles with GUI (Graphical User Interface) means, such as a mouse, virtual sliders, and so on.

Once the desired virtual model is complete, the insoles model is ready to be sent to a production center, a production apparatus 60, and the like.

FIG. 6 schematically illustrates an apparatus for fitting insoles to a patient's feet, according to embodiments of the present invention.

The difference between the embodiment illustrated in FIG. 1 and that of FIG. 6 is the presence of the production apparatus 60, which produces insoles according to the design prepared by apparatus 2. The design of the insoles may be provided by wire 28, USB drive, wireless means (such as RF, Bluetooth), and so on.

Insole production systems are well known, and they operate at an insole production center. The advantage the present invention provides is producing insoles at the same location where the foot measurement takes place.

As mentioned above, the term "strain" refers in the text and claims herein to any expression of weight.

In the figures and/or description herein, the following numerals have been mentioned:

Numeral 2 denotes an apparatus for fitting insoles to a patient, according to preferred embodiments of the present invention.

numeral 4 denotes a display;
numeral 6 denotes a fitting panel for the right foot;
numeral 8 denotes a fitting panel for the left foot;
numeral 10 denotes a cable connecting the fitting units with computer 12;
numeral 12 denotes a computer;
numeral 14 denotes a display of the computer;
numeral 16 denotes a region of a patient's sole in which the strain thereof is "normal";
numeral 18 denotes a region of a patient's sole in which the strain thereof is "abnormal" (overstrain or under strain);
numeral 20 denotes a presentation of the strains on the right foot of a patient;
numeral 22 denotes a presentation of the strains on the left foot of a patient;
numeral 24 denotes a foot;
numeral 26 denotes a pad, preferably of flexible material;
numeral 28 denotes a data connection wire between apparatus 2 and apparatus 60;
numeral 30 denotes an elevating unit;
numeral 32 denotes a cylinder of a fitting unit;
numeral 34 denotes a piston of a fitting unit;
numeral 36 denotes a ball used as a bearing;
numeral 38 denotes a platform of a fitting unit;
numeral 40 denotes a strain sensor;
numeral 50 denotes a fitting unit; and
numeral 60 denotes an apparatus for producing insoles.

While certain features of the invention have been illustrated and described herein, the invention can be embodied in other forms, ways, modifications, substitutions, changes, equivalents, and so forth. The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An apparatus for fitting an insole to correlate with a virtual model of desired strains on each of a plurality of points of the plantar surface of a patient, the apparatus comprising:
    a first fitting panel, comprising:
        a virtual model of desired strains on each of a plurality of points of the plantar surface of a foot wherein said virtual model can take into consideration input variables relating to specific orthopedic problems, foot size, left foot or right foot indication;
        a plurality of fitting units deployed on said first panel, thereby constituting a temporal tangible insole for both measuring the strains applied on each of said plurality of points of said plantar surface of a foot while standing on said temporal insole, and for comparing and adjusting the measured strain to correlate with the strain of the corresponding point in said virtual model, each fitting unit comprising:
            (a) a strain sensor, for measuring the strain applied, by the corresponding point of the plantar surface of said foot on said fitting unit; and
            (b) an elevating unit, for elevating the top point of said fitting unit to a desired point in which the measured strain corresponds to the desired strain on said point of the plantar surface;
        a processing unit, for repeating a process of measuring, comparing, and adjusting the strains measured on each of said plurality of points of said temporal tangible insole to correlate with the corresponding desired strain as indicated by said virtual model of desired strains,
    wherein said process of adjusting comprises instructing each of said elevating unit to adjust the elevation of the top point thereof towards a position wherein the strain of said foot, as measured by said strain sensor, corresponds to the strain of said virtual model,
    thereby upon ending said process for all of said plurality of points of the temporal tangible insole, the pressure applied on each of said plurality of points corresponds to the desired strain as indicated by said virtual model, and automatically defines said insole according to said temporal tangible insole without any necessary intervention of an expert.

2. An apparatus according to claim 1, further comprising a second fitting panel in the structure of said first fitting panel, for enabling fitting insoles to feet of different length.

3. An apparatus according to claim 1, further comprising a unit for producing an insole.

4. An apparatus according to claim 1, wherein said first fitting panel further comprises elevated edges, for placing said foot in a predefined position on said panel.

5. An apparatus according to claim 1, wherein the position of said foot on said panel is detected by computerized means.

6. An apparatus according to claim 1, wherein said elevating unit is operated by hydraulic means.

7. An apparatus according to claim 1, wherein said elevating unit is operated by pneumatic means.

8. An apparatus according to claim 1, further comprising a user interface, for adjusting a designed insole.

9. An apparatus according to claim 1, further comprising a display, for displaying information selected from a group comprising: measured strains, designed insole.

10. An apparatus according to claim 1, further comprising a pad placed on said fitting units.

11. An apparatus according to claim 1, wherein each of said fitting units comprises on the top thereof a platform movable along a bearing, thereby fitting the position of said platform according to the plantar surface thereof.

12. An apparatus according to claim 1, wherein said fitting units are deployed in a matrix order.

13. An apparatus according to claim 1, wherein the deployment of said fitting units corresponds to the plantar surface of a common patient.

14. An apparatus according to claim 1, wherein said virtual model is selected from a library of virtual models.

15. An apparatus according to claim 1, wherein said virtual model is generated by employing at east one variable.

16. An apparatus according to claim 15, wherein said at east one variable is selected from a group comprising: identification of an orthopedic problem, foot size, left foot or right foot.

17. A method for fitting an insole to correlate with a virtual model of desired strains on each of a plurality of points of the plantar surface of a patient, the method comprising the steps of:
    providing a virtual model of desired strains on each of a plurality of points of a plantar surface of a foot wherein said virtual model can take into consideration input variables relating to specific orthopedic problems, foot size, left foot or right foot indication;
    providing a plurality of fitting units, each comprising both strain sensor and elevating unit, deployed on a first panel, thereby constituting a temporal tangible insole for both measuring the strain applied on each of said plurality of points of said plantar surface of a foot while standing on said temporal insole, and for comparing and adjusting the measured strain to correlate with the strain of the corresponding point in said virtual model, repeating the process of:
(a) comparing the strain, applied by each of said plurality of points of the plantar surface of said patient on a corresponding strain sensor, with the optimal strain to be applied according to the corresponding point of said virtual model; and
(b) adjusting the elevation of each of said strain sensors, comparing to the corresponding points of the plantar surface of said patient, towards a position wherein the measured strain by each of said strain sensors will correspond to the optimal strain to be applied according to the corresponding point of said virtual model,
until the strain measured on each of said plurality of points of said temporal tangible insole correlates with the corresponding desired strain as indicated by said virtual model of desired strains,
thereby upon ending said process for all of said plurality of points of the temporal tangible insole, the pressure applied on each of said plurality of points corresponds to the desired strain as indicated by said virtual model,
thus automatically defining said insole according to said temporal tangible insole without any necessary intervention of an expert.

18. A method according to claim 17, wherein said adjusting is carried out by increasing said elevation in the event the measured strain of a point is less than the corresponding strain of said model, and vice versa.

19. A method for fitting insoles to correlate with a virtual model of desired strains on each of a plurality of points of the plantar surface of a patient, the method comprising the steps of:
providing a virtual model of desired strains on each of a plurality of points of the left and right plantar surfaces of a patient's feet wherein said virtual model can take into consideration input variables relating to specific orthopedic problems, foot size, left foot or right foot indication;
providing a plurality of fitting units, each comprising both strain sensor and elevating unit, deployed on first and second panels, thereby constituting temporal tangible insoles for both measuring the strain applied on each of said plurality of points of said plantar surfaces of a patient's feet while standing on said temporal insoles, and for comparing and adjusting the measured strain to correlate with the strain of the corresponding point in said virtual model,
adjusting the elevation of each of said strain sensors, comparing to the corresponding points of the plantar surfaces of said patient, until the total strains of the left foot equals the total stains of the right foot;
for each foot repeating the process of:
(a) comparing the strain, applied by each of said plurality of points of the plantar surface of said patient on a corresponding strain sensor, with the optimal strain to be applied according to the corresponding point of said virtual model; and
(b) adjusting the elevation of each of said strain sensors, comparing to the corresponding points of the plantar surface of said patient, towards a position wherein the measured strain by each of said strain sensors will correspond to the optimal strain to be applied according to the corresponding point of said virtual model;
until the strain measured on each of said plurality of points of said temporal tangible insoles correlates with the corresponding desired strain as indicated by said virtual model of desired strains,
thereby upon ending said process for all of said plurality of points of the temporal tangible insoles, the pressure applied on each of said plurality of points corresponds to the desired strain as indicated by said virtual model,
thus automatically defining said insoles according to said temporal tangible insoles without any necessary intervention of an expert.

20. A method according to claim 19, wherein said adjusting is carried out by increasing said elevation in the event the measured strain of a point is less than the corresponding strain of said model, and vice versa.

* * * * *